(12) United States Patent
Aberg

(10) Patent No.: US 6,372,799 B1
(45) Date of Patent: Apr. 16, 2002

(54) NON-SEDATING DIPHENHYDRAMINE METABOLITES

(75) Inventor: A. K. Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 09/744,458

(22) PCT Filed: Aug. 11, 1999

(86) PCT No.: PCT/US99/18257

§ 371 Date: Feb. 8, 2001

§ 102(e) Date: Feb. 8, 2001

(87) PCT Pub. No.: WO00/08928

PCT Pub. Date: Feb. 24, 2000

Related U.S. Application Data

(60) Provisional application No. 60/096,366, filed on Aug. 13, 1998.

(51) Int. Cl.⁷ ............................................. A61K 31/135
(52) U.S. Cl. ....................................................... 514/648
(58) Field of Search .......................................... 514/648

(56) References Cited

PUBLICATIONS

Database CA on STN AN: 106169, Andreau, Spain, "Aryl–substituted Isopropylamines" Abstract to ES 420193 A1, Jun. 16, 1976.

J. Clin. Pharmacol 1986; 26: 529–533; "Pharmacokinestics of Diphenydraine and a Demethylated Metabolite Following Intravenous and Oral Administration"; Blyden, et al.

*Primary Examiner*—Dwayne C. Jones
(74) *Attorney, Agent, or Firm*—Nields & Lemack

(57) ABSTRACT

Disclosed are N-substituted metabolites of diphenhydramine, which have been found to be potent and orally active antihistaminic compounds that are devoid of sedative side effects. Phamaceutically acceptable salts of the compounds, a complex with 8-chlorotheo-phylline, therapeutic use and compositions containing the compounds are also described.

18 Claims, No Drawings

NON-SEDATING DIPHENHYDRAMINE METABOLITES

This application is a 371 of PCT/US99/18257, filed on Aug. 11, 1999, and claims benefit of provisional application No. 60/096,366, filed Aug. 13, 1998.

TECHNICAL FIELD

This invention relates to new chemical entities as shown below and to methods of treatment of disease states modulated by allergic, inflammatory, or cholinergic activities in a mammal, using said new chemical entities.

The compounds of the invention include chemical entities of the following Formula I

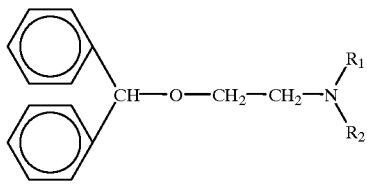

where $R_1$ is H and $R_2$ is H or methyl, and the pharmaceutically acceptable salts thereof.

The compounds of this inventions have been found to possess pharmacological properties that render said compounds to be useful in treating allergies, inflammations, various types of ocular diseases (such as for example vernal conjunctivitis and allergic conjunctivitis), different types of smooth muscle hyperreactivity (such as for example bronchial hyperreactivity) and asthma or other diseases that are mediated through histaminic receptors of various types.

More particularly, this invention relates to entities and to methods of treating allergic disorders (such as for example allergic rhinitis), motion sickness, pulmonary disorders (such as for example asthma, bronchitis, cough and bronchial hyperreactivity), skin disorders (such as for example urticaria, psoriasis and atopic dermatitis), gastrointestinal disorders (such as for example hypersecretory syndromes including Zollinger-Ellison syndrome, gastric irritation and enteritis), and other inflammatory disorders and/or allergic disorders (such as for example ocular conjunctivitis and ocular keratitis), while avoiding side effects (such as sedation, cardiac arrhythmias and ocular irritation), using said chemical entities.

The invention also refers to compositions, containing at least one of said chemical entities and combinations of the present compounds with various other chemical entities.

BACKGROUND OF THE INVENTION

This invention relates specifically to anti-allergic and anti-inflammatory compounds, having therapeutic use in various diseases, most importantly for patients suffering from allergies, including urticaria, atopic dermatitis, allergic rhinitis, ocular conjunctivitis and keratitis.

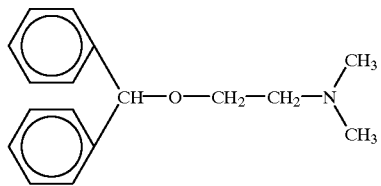

Formula 2. DIPHENHYDRAMINE

The present compounds demonstrate chemical similarities to diphenhydramine (Benadryl®) and dimenhydrinate (Dramamine®) and the secondary amine ($R_1$=H; $R_2$=Me; see FIG. 1) has been described in the prior art as a naturally occurring metabolites of diphenhydramine. Sedative side effects have severely limited the therapeutic usefulness of diphenhydramine and such side effects can been reduced or eliminated by using the compounds of the present invention.

SUMMARY OF THE INVENTION

The present invention is concerned with chemical entities as described below, methods of using said chemical entities for therapeutic purposes and compositions containing a therapeutically effective amount of at least one compound or a pharmaceutically acceptable acid addition salts thereof, having the formula:

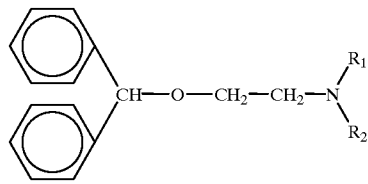

where $R_1$ H and $R_2$ is H or methyl, and the pharmaceutically acceptable salts thereof.

The compounds of the present invention have been synthesized according to methods that are well known to those skilled in the art.

The compounds of this invention have also been studied biologically. Significant differences are found between the compounds of the present invention and diphenhydramine. Thus, diphenhydramine has profound sedative side effects while the compounds of the present invention have no detectable sedative activity. The antihistaminic activities of the compounds have been investigated, using the methodology described below.

DETAILED DESCRIPTION

BIOLOGICAL STUDIES OF THE COMPOUNDS OF THE PRESENT INVENTION

As discussed above, it is now shown that the compounds of the present invention have beneficial pharmacological effects, useful in the treatment of various disorders, such as allergies and ocular disorders. As described in the following biological studies, it has now been found that the primary and secondary amine metabolites of the severely sedating 1st generation antihistamine diphenhydramine are potent antihistamines that are devoid of the sedative side effects of diphenhydramine.

1. Antihistaminic Effects in vitro

The affinities of the test compounds for histamine $H_1$-receptors are assessed using the [$^3$H]pyrilamine binding assay, modified after Chang et al. Heterogeneity of Histamine $H_1$-Receptors. J. Neurochem. 1979, 32: 1653–1663. Briefly, membranes from bovine cerebellum are incubated with [$^3$H]pyrilamine and the test compound at increasing concentrations. The specific binding of the radioactive ligand to the receptor is defined as the difference between total binding and nonspecific binding, determined in the presence of an excess of unlabelled ligand. $IC_{50}$ values (concentration required to inhibit 50% of specific binding of [$^3$H]pyrilamine) are determined by non linear regression analysis of the competition curves.

2. Antihistaminic Effects in vivo

The dorsal hair of male rats weighing 150–200 g are clipped and depilated. Animals are starved overnight and administered orally with the test compound, vehicle or reference compound. Four dorsal test areas are marked with permanent ink, carefully avoiding the area closest to the spine. Exactly sixty minutes after the oral administration of the test compound, two intradermal injections of histamine (50 μL injection of 1.0 mg/ml of histamine dihydrochloride) are performed, one on each side on the back of the animal. Two intradermal injections of the vehicle for the histamine solution are also injected intradermally to each animal. Evans blue dye (20 mg/kg at 1.0 mg/kg) is injected intravenously one minute prior to the expiration of the pretreatment time. Twenty minutes are allowed for the wheal response to fully develop, whereupon the animals are euthanized and an incision is made along the spine. The dorsal skin containing the intradermal wheals is then deflected. The blue spotted areas are measured in millimeters and the duplicate vehicle wheal responses are averaged. Mean values, standard errors and statistical significance are calculated. In vehicle-treated animals, the wheal area is on an average increased by histamine by approximately 70 $mm^2$. In animals pretreated with an active antihistaminic compound, the histamine-induced response is less than that of vehicle-treated animals. The inhibition is calculated in percent.

3. Studies on Sedative Effects in vivo

The physostigmine-induced lethality test is being used in the present studies. This test is a modification of the sedation test technique reported by VILLANI et al., in U.S. Pat. No. 4,659,716. In short, physostigmine (1.9 mg/kg s.c.) produces 90–100% lethality when given to grouped mice with 10 animals in each plastic cage (approx. 11×26×13 cm). Mice administered a sedating agent, such as for example a sedative antihistamine prior to physostigmine are protected and survive. In the present study, test compounds are administered orally 60 minutes prior to physostigmine. The number of survivors is counted 30 minutes after physostigmine administration.

The present invention provides the therapeutic use of the two compounds described above, including the pharmaceutically acceptable acid addition salt and solvates of said compounds.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include but are not limited to acetic, benzenesulfonic (besylate), benzoic, chlorotheophylline, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. Hydrochloride and chlorotheophylline salt forms are particularly preferred.

The present invention also provides pharmaceutical compositions, which comprise at least one compound of the invention, formulated together with one or more pharmaceutically acceptable carriers. The pharmaceutical compositions may be specially formulated for oral administration, conjunctival instillation, sublingual administration, parenteral administration, dermal or transdermal administration, rectal administration, nasal administration, buccal administration, or for topical administration, or for administration by inhalation.

Pharmaceutical compositions of this invention can be administered to humans and other mammals by various routes, including, but not limited to oral, sublingual, perilingual, parenteral, cutaneous, transdermal, rectal, buccal, topical, by conjunctival or ocular instillation, or as an oral spray or aerosol, or by nasal administration.

Oral Administration Forms

Pharmaceutical compositions of this invention for oral administration of solid dosage forms, include capsules, granules, pills, powders, and tablets. In such solid dosage forms, the active compound may be mixed with one or more pharmaceutically acceptable excipients or carriers (ex. sodium citrate, dicalcium phosphate), fillers or extenders (ex starch, lactose, sucrose, glucose, mannitol, silicic acid), binders (ex. carboxymethylcellulose, alginates, gelatin, polyvinylpyrrolidone, sucrose, acacia), humectants (ex. glycerol), solution retarding agents (ex. paraffin), disintegrating agents (ex. agar-agar, calcium carbonate, starch, alginic acid, silicates sodium carbonate), absorption accelerators (ex. quaternary ammonium compounds), wetting agents (ex. cetyl alcohol, glycerol monostearate), absorbents (ex. kaolin, bentonite clay), lubricating agents (ex. talk, calcium stearate, magnesium stearate, polyethylene glycols, sodium lauryl sulfate), and/or buffering agents.

Solid forms of capsules, dragees, granules, pills, and tablets can have coatings and/or shells (ex. enteric coatings) known in the pharmaceutical formulating art. The compositions may also be designed to release the active ingredient (s) in a certain part of the gastrointestinal tract or in a controlled release, slow-release or in a delayed-release manner.

The composition may also be designed for lymphatic absorption of the active ingredient(s).

The active compound(s) can also be micro-encapsulated with one or more of the above-mentioned excipients.

Liquid dosage forms for oral administration include pharmaceutically acceptable emulsions, solutions, suspensions, syrups and elixirs. The liquid dosage form may also contain commonly known diluents (ex. water, other solvents, solubilizing agents), emulsifiers (ex. ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof.

Besides inert diluents, the oral compositions can also include adjuvants such as wetting, emulsifying, suspending, sweetening, or flavoring agents.

Suspensions may contain one or more suspending agents known in the pharmaceutical formulating art.

Topical Administration Forms (Including forms for ocular and conjunctival administration,)

Compositions for topical, ocular or conjunctival application of the compounds of this invention include but are not limited to solutions, suspensions, droplets, sprays, gels, creams, ointments and powders.

In addition to the therapeutically active ingredients, the composition of this invention for topical, ocular or conjunctival administration may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, ONAMER M and other agents known to those skilled in the art. Such preservatives, if utilized, will typically be employed in an amount from 0.001% to 1.0% by weight (wt. %). Examples of suitable agents which may be utilized to adjust the tonicity or osmolality of the formulations include sodium chloride, potassium chloride, mannitol, dextrose glycerin and propylene glycol. Such agents, if utilized, will be employed in an amount of 0.1% to 10.0% by weight (wt. %). The compositions are preferably aqueous, and have a pH in the range of 3.5 to 8.0.

As realized by those skilled in the art, compositions may be formulated in various dosage forms suitable for topical ophthalmic delivery, including solutions, suspensions, emulsions, gels, and erodible solid ocular inserts.

Parenteral Administration Forms

The term "parenteral" administration includes intravenous, intraarterial, intramuscular, intraperitoneal, intracutaneous, subcutaneous and intraarticular injection or infusion. Pharmaceutical compositions for parenteral injections include pharmaceutically acceptable sterile aqueous or non-aqueous solutions, dispersions, suspensions, emulsions and sterile powders for reconstitution into sterile injectable solutions or dispersions prior to use. Various aqueous and non-aqueous carriers, diluents solvents and vehicles may be used (ex. water, ethanol, glycerol, glycol), as well as vegetable oils (ex. olive oil), and organic esters (ex ethyl oleate), or mixtures thereof may be used. Fluidity can be maintained by use of coating material such as lecithin, by restricting particle size and by use of surfactants.

The compositions may also contain adjuvants such as preservatives, wetting agents, emulsifying agents, dispersing agents, antibacterial agents, antifungal agents, isotonic agents, and/or absorption-delaying agents. Absorption-prolonging or absorption-slowing effects may be achieved by injecting a crystalline or amorphous suspension with low water solubility. Delayed absorption may also be obtained by dissolving or suspending the drug in an oil vehicle or by using injectable depot forms (ex. microencapsulated matrices of the drug in biodegradable polymers, such as polylactide-polyglycolide, polyorthoesters, polyanhydrides) or by using various types of liposomes or microemulsions to hold the drug. Formulations for injection can be sterilized by various methods, as known lo those skilled in the art.

Rectal Administration Forms

Compositions for rectal administration are preferably suppositories.

Buccal Administration Forms

Compositions for buccal administration include sublingual preparations, mouthwashes, chewing gums, toothpastes, etc.

Sublingual Administration Forms

Various galenic formulations can be used, as for example: concentrated solutions or suspensions of the drug that may be applied into the mouth by various drop devices or various aerosol devices may be used to spray the drug onto the oral mucus membranes or specifically designed controlled release tablets, capsules, gels, chewing preparations or powders may as well be used for fast or delayed delivery of the full dose. Compositions for sublingual administration may also contain taste-modifying agents.

Transdermal Administration Forms

The term "transdermal" includes the use of various devices ("patches" etc.) or chemicals, such as for example dimethylsulphoxide (DMSO) that may facilitate or modify the transport or absorption of the drug through the skin. Compositions for transdermal administration of the compounds of this invention include various known patches, bandages, other delivery systems, penetration-promoting agents, etc.

Oral or Nasal Spray or Droplet Administration

Compositions for oral or nasal sprays or droplets may be in the form of solutions, suspensions or dry powders and may be designed for nasal, buccal, bronchial/pulmonary, and/or gastric absorption of the drug.

Therapeutic Dose Levels.

The actual dosage levels of active ingredients in the pharmaceutical compositions of this invention may be varied so as to obtain the desired therapeutic effect. Thus the amount of drug used varies and may depend on factors such as administration form, severity of the disease, frequency of dosing etc. For use as medication to patients suffering from various medical disorders, the oral doses of the compound of this invention are used at dose levels of 0.5 mg to about 200 mg, preferably from 5 mg to 60 mg once to four times daily to a patient weighing 60 kg. The daily dose may be increased or decreased depending on various factors, for example the weight and the disease status of the patient. It may be necessary to use dosages outside these ranges, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat an allergic reaction" are encompassed by the above-described dosage amounts and dose frequency schedule.

As examples, for use as medication to patients suffering from allergic rhinitis, oral doses of the compound of this invention are used at dose levels of 1 mg to about 100 mg, preferably from 5 mg to 60 mg, once to four times daily to a patient weighing 60 kg. For use as medication to patients suffering from seasonal allergic conjunctivitis, the concentration of a solution for instillation into the conjunctival sac ranges from 0.01% to 2.0%, preferably 0.02% to 1.0%, once to six times daily to a patient weighing 60 kg.

Oral Unit Dosage Formulation.

Because of their ease of administration, tablets and capsules represent some of the most advantageous oral dosage unit forms, in which case solid pharmaceutical carriers are employed. For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. If desired, tablets may be coated by standard aqueous or nonaqueous techniques. Tablets and capsuls may also be given one or more colors that may facilitate the recognition of the tablet or capsule. All of the foregoing techniques are well know to persons of skill in the pharmaceutical art. Each tablet may preferably contain from about 0.5 mg to about 60 mg of the active ingredient. The following examples demonstrate how tablets and capsules may be formulated.

For tablets, the active ingredient is sieved through a suitable sieve and blended with the lactose until a uniform blend is formed. Suitable volumes of water are added and the powders are granulated. After drying, the granules are then screened and blended with the magnesium stearate. The resulting granules are then compressed into tablets of desired shape. Tablets of other strengths may be prepared by altering the ratio of active ingredient to the excipient(s) or the compression weight.

Oral Formulation - Tablets.

| Formula | Quantity per Tablet in mg. | | |
|---|---|---|---|
|  | Tablet A | Tablet B | Tablet C |
| Active ingredient according to Claim 3 | 5.0 | 10.0 | 20.0 |
| Lactose BP | 148.5 | 143.5 | 133.5 |
| Starch BP | 30.0 | 30.0 | 30.0 |
| Pregelatinized Maize Starch BP | 15.0 | 15.0 | 15.0 |
| Magnesium Stearate | 1.5 | 1.5 | 1.5 |
| Compression Weight | 200.0 | 200.0 | 200.0 |

Oral Formulation - Capsules

| Formula | Quantity per Capsule in mg. | | |
|---|---|---|---|
|  | Capsule A | Capsule B | Capsule C |
| Active ingredient according to Claim 3 | 5.0 | 10.0 | 20.0 |
| Starch 1500 | 94.0 | 89.0 | 79.0 |
| Magnesium Stearate BP | 1.0 | 1.0 | 1.0 |
| Compression Weight | 100.0 | 100.0 | 100.0 |

For capsules, the active ingredient is sieved and blended with the excipients. The mixture is filled into suitably sized two-piece hard gelatin capsules using suitable machinery. Other doses may be prepared by altering the fill weight and if necessary, changing the capsule size to suit.

In addition to the common dosage forms set out above, the compounds of the present invention may also be administered by controlled release means and delivery devices such as for example those described in U.S. Pat. Nos.: 2,538,127; 3,536,809; 3,598,123; 3,845,770; 3,916,899; 4,008,719; 4,698,359; 5,250,287; 5,464,387; 5,693,608 and PCT application WO92/20377, the disclosures of which are hereby incorporated by reference.

This invention provides methods for the treatment and/or prophylaxis of all forms of allergic rhinitis, allergic bronchitis, multi-system allergies, allergic skin disorders, allergic ocular/conjunctival disorders and other disorders that are mediated by histamine in mammals, such as humans, while avoiding sedating side effects and other toxic manifestations of diphenhydramine. These methods comprise administering to the mammal in need of such treatment and/or prophylaxis, effective amounts of at least one compound of the invention or a pharmaceutically acceptable salt thereof or an equi-molar complex consisting of a compound of the present invention and 8-chlorotheophylline.

On another aspect, the present invention provides methods for increasing the sensitivity of a tumor to an antineoplastic agent when the tumor is resistant to the antineoplastic agent by administering to the subject harboring the resistant tumor a compound of the present invention as a potentiating agent concurrently with an antineoplastic agent. Resistance to the antineoplastic agent may be an intrinsic property of the tumor or develop in response to prior treatment with the same antineoplastic agent or to another antineoplastic agent. An aspect of this invention is a method of selectively inhibiting the growth of tumor cells in a subject in need of such treatment by concurrently administering to the subject an antineoplastic agent and a compound of this invention as a potentiating agent. The potentiating agent is administered in an amount effective to reduce the amount of the antineoplastic agent required to achieve the same growth inhibiting effect on the tumor cells by the antineoplastic agent achieved without the concurrent administration of the potentiating agent; or inhibit the development of multiple drug resistance in the tumor cells after treatment with the antineoplastic agent over time. Another aspect of the present invention is a method of inhibiting multiple drug resistance in a subject in need of such treatment by administering the subject a potentiating agent in an amount effective to combat multiple drug resistance.

This invention also provides methods for co-administration of a compounds of the invention with adrenergic beta-receptor agonists, including but not limited to albuterol, terbutaline, fenoterol, formoterol or salmeterol, thereby eliminating or decreasing bronchial hyperreactivity that may be induced by said beta-agonist therapy. The invention also provides methods for co-administration of a compound of this invention with other agents or drugs causing bronchial hyperreactivity, including but not limited to adrenergic beta-receptor blocking agents or cyclooxygenase inhibitors, thereby eliminating or decreasing the bronchial hyperreactivity that is induced by such therapy.

This invention also provides methods for co-administration of a compound of this invention, with at least one drug of the following classes: ocular antihypertensive agents, adrenergic agonists or antagonists, agents with cholinergic activities, antibacterial agents, antiviral agents, steroids, cyclooxygenase inhibitors, leukotriene antagonists, lipoxygenase inhibitors and other ocular therapeutic remedies. In particular, the present invention provides for co-administration of a compound of this invention with ophthalmic decongestants, such as for example phenylephedrine, naphazoline, tetrahydrozoline or with antibacterial agents, such as bacitracin, neomycin and polymyxin.

This invention also provides methods for treating cough, cold, cold-like or flu symptoms and the discomfort, headache, pain, fever and general malaise associated therewith, in a mammal, while avoiding the concomitant liability of adverse side-effects selected from the group consisting of sedation, memory impairment, cardiodepression, and arrhythmogenicity comprising administering to said mammal a composition, said composition comprising (i) a therapeutically active amount of a compound of the invention, or a pharmaceutically acceptable salt thereof, together with one or more compounds of the class consisting on non-steroidal antiinflammatory agents, non-narcotic analgesics, decongestants, cough suppressants, wetting agents, aromatic agents, expectorants and water.

This invention also provides methods for treating nausea, vomiting, dizziness, vertigo [including peripheral (labyrinthine) vertigo], and motion sickness, while avoiding the concomitant liability of adverse side-effects selected from the group consisting of sedation, memory impairment, cardiodepression, and arrhythmogenicity comprising administering to said mammal a complex, said complex comprising (i) a therapeutically active amount of a compound of the invention, or a pharmaceutically acceptable salt thereof or (ii) a complex, consisting of a therapeutically active amount of a compound of the invention, or a pharmaceutically acceptable salt thereof, and an equimolar amount of 8-chlorotheophylline.

Methods of Making the Chemical Entities of the Invention

Desmethyl-diphenhydramine HCl:

A mixture of 2-diphenylmethyloxy-ethyl chloride (1.6 g), methyl-amine (40 mL of 2.0 M solution in methanol) in methanol (20 mL) was heated at 100° C. in a seal-tube for 15 hrs. The reaction mixture was concentrated and the residue was purified by silicon gel column chromatography using methanol/chloroform (5:100) as eluent to give 0.6 grams of pure product (colorless oil) as free base. The free base (0.56 g) was dissolved in dioxane (15 mL), and 5 mL of 6.8 M IICl in dioxane was added slowly by cooling with ice bath. The solvent was evaporated to give white solid (640 mg), m.p. 156–158° C.

Didesmethyl-diphenhydramine HCl:

2-Diphenylmethyloxy-ethyl chloride (3.66 grams, 10 mmol) is dissolved in methanol saturated at room temperature with ammonia (50 mL). After heating in a sealed tube at 100° C. for 15 hrs, the solution is evaporated to dryness, and the residue is purified by chromatography on silica gel with 10% methanol in chloroform as eluent to give the product as the free base. The base is dissolved in dioxane (25–40 mL) and a solution of 6.8 M hydrogen chloride in dioxane (10–15 mL) is added slowly with cooling in ice. Evaporation of the solvent gives 2.3–2.7 grams of the title compound as a white solid (ca. 60–70% yield).

EQUIVALENTS

Those skilled in the art will recognize, or be able to ascertain, using no more than routine experimentation, many equivalents to the specific embodiments of the invention described herein. Such equivalents include numerous pharmaceutically acceptable salt forms e.g. sulfate, fumarate, hydrobromide, hydrochloride, dihydrochloride, methanesulphonate, hydroxynaphthoate, chlorotheophyllin or where appropriate one or other of the hydrate forms thereof, see Merck Index 11th edition (1989) items 9089, 209, 3927, 4628, 8223, 5053, 5836, 8142, 2347, 7765, 1840, 9720, 7461, 1317, 4159, and 963 and references cited therein and Am. Rev. Resp. Dis. 1988, 137: (4;2/2) 32. Such equivalents also include the co-administration of at least one compound of the present invention with any other drug that is used to combat diseases in mammals, mentioned in this document. Such equivalents also include the co-administration of at least one compound of the present invention with any other compound or drug that may be used in combination with diphenhydramine. Those skilled in the art of medicine will also realize that higher or lower doses than those indicated here may be preferred and the doses may be given more or less frequently than suggested here.

Those skilled in the art, will realize that 8-chlorotheophylline, as used here in a complex with a compound of the invention, may be substituted with compounds that are chemically or pharmacologically related to 8-chlorotheophylline.

Those skilled in the art of pharmacology, will realize that the compounds of the invention, having certain pharmacological properties (such as antihistaminic activity on various receptor types, antimuscarinic activity, PAF-antagonistic activity, mast cell stabilizing activity etc.) may be useful for other indications than those listed here. Such indications are equivalents to the specific embodiments of the invention described herein. All equivalents are intended to be included in this present invention.

What is claimed is:

1. A method for treating allergic or cholinergic disorders in a mammal, comprising administering to a mammal a therapeutically effective amount of a compound having the following formula:

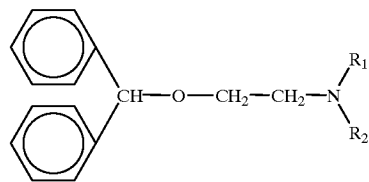

where $R_1$ is H and $R_2$ is H or methyl, and pharmaceutically acceptable salts thereof, together with a pharmaceutically acceptable carrier.

2. The method of claim 1 wherein said compound is administered as a complex (1:1) with 8-chlorotheophylline.

3. The method of claim 1 wherein said allergic disorder is selected from the group consisting of allergic rhinitis, bronchitis, urticaria, atopic dermatitis, allergic asthma and enteritis.

4. The method of claim 1 wherein said cholinergic disorder is selected from the group consisting of nausea, vomiting, dizziness, vertigo and motion sickness.

5. A method of treating ocular disorders in a mammal, comprising administering to said mammal a therapeutically effective amount of a compound having the following formula:

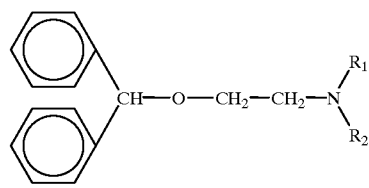

where $R_1$ is H and $R_2$ is H or methyl, and pharmaceutically acceptable salts thereof, together with a pharmaceutically acceptable carrier.

6. The method of claim 5, wherein said ocular disorder is selected from the group consisting of anterior uveitis, blepharitis, conjunctivitis, cranial arteritis, endophthalmitis, episcleritis, keratitis, keratoconjunctivitis, optic neuritis, posterior uveitis, retinopathy and scleritis.

7. A method of treating respiratory disorders in a mammal, comprising administering to said mammal a thera peutically effective amount of a compound having the following formula:

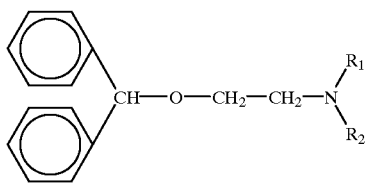

where $R_1$ is H and $R_2$ is H or methyl, and pharmaceutically acceptable salts thereof, together with a pharmaceutically acceptable carrier.

8. The method of claim 7, wherein said respiratory disorder is selected from the group consisting of chronic obstructive pulmonary disease (COPD), asthma, cough, bronchitis, common cold and influenza.

9. A method of treating gastrointestinal disorders in a mammal, comprising administering to said mammal a therapeutically effective amount of a compound having the following formula:

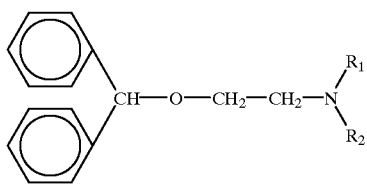

where $R_1$ is H and $R_2$ is H or methyl, and pharmaceutically acceptable salts thereof, together with a pharmaceutically acceptable carrier.

10. The method of claim 9, wherein said gastrointestinal disorder is selected from the group consisting of hypersecretory syndrome, the Zollinger-Ellison syndrome, gastric irritation, enteritis, gastric ulcer, acid indigestion and heartburn.

11. The method of increasing the sensitivity of a tumor in a subject, said tumor being resistant or partly resistance to an antineoplastic agent, said method comprising concurrently administering to said subject said antineoplastic agent and a potentiating agent having the following formula:

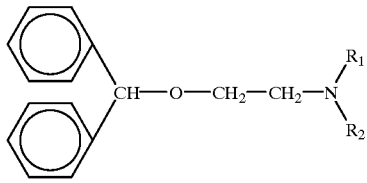

where $R_1$ is H and $R_2$ is H or methyl, and pharmaceutically acceptable salts thereof, together with a pharmaceutically acceptable carrier.

12. The method of treating cough, cold, cold-lie or flu symptoms and the discomfort, headache, pain, fever or general malaise associated therewith in a mammal while avoiding the concomitant liability of adverse side-effects selected from the group consisting of sedation, memory impairment, cardiodepression, arrhythmogenicity, dry mouth and blurry vision, comprising administering to said mammal a composition comprising a therapeutically effective amount of a compound having the following formula:

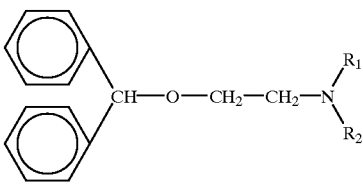

where $R_1$ is H and $R_2$ is H or methyl, and pharmaceutically acceptable salts thereof, together with one or more drugs of the class consisting of antiinflammatory agents, analgesics, decongestants, cough suppressants and expectorants, together with a pharmaceutically acceptable carrier.

13. The method of claim 1, 5, 7, 9, 11 or 12, wherein said compound is administered by a route selected from the group consisting of inhalation, conjunctival instillation, nasal instillation, insufflation, parenteral administration, dermal administration, transdermal administration, buccal administration, rectal administration, sublingual administration, perilingual administration, nasal administration, topical administration and oral administration.

14. The method of claim 1, 5, 7, 9, 11 or 12, wherein said compound is administered by a delayed release formulation.

15. The method of claim 1, 5, 7, 9, 11 or 12 wherein said compound is administered in an amount from about 0.2 mg to about 200 mg one to four times daily.

16. The method of claim 1, 5, 7, 9, 11 or 12, wherein said compound is administered by conjunctival instillation of a solution containing from about 0.01% to about 2.0% of said compound, one to six times daily.

17. A solid, semi-solid, liquid, suspension, aerosol or transdermal pharmaceutical composition, comprising a therapeutically effective amount of a compound having the following formula:

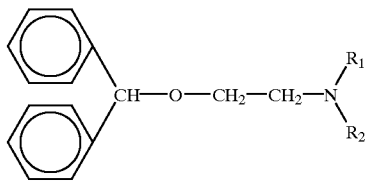

where $R_1$ is H and $R_2$ is H or methyl, and pharmaceutically acceptable salts thereof, in combination with a pharmaceutically acceptable carrier or carrier system that facilitates dermal or transdermal delivery of said compound.

18. A method comprising topically administering to an eye of a mammal in need thereof a composition comprising a therapeutically effective amount of a compound having the following formula:

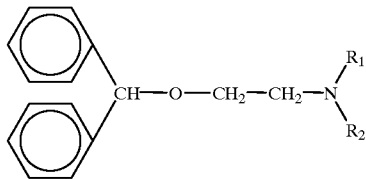

where $R_1$ is H and $R_2$ is H or methyl, and pharmaceutically acceptable salts thereof, together with one or more drugs selected from the group consisting of cholinergic agents, anti-muscarinic agents, choline esterase inhibitors, adrenergic beta-receptor blocking agents, anti-bacterial agents, sympathomimetics, carbonic anhydrase inhibitors, antiinflammatory agents, decongestants, astringents, viscosity adjusting substances and topical anesthetics.

* * * * *